(12) United States Patent
Karpov et al.

(10) Patent No.: US 9,149,799 B2
(45) Date of Patent: Oct. 6, 2015

(54) EGGSHELL CATALYST CONSISTING OF A HOLLOW CYLINDRICAL SUPPORT BODY AND A CATALYTICALLY ACTIVE OXIDE MATERIAL APPLIED TO THE OUTER SURFACE OF THE SUPPORT BODY

(75) Inventors: Andrey Karpov, Mannheim (DE); Catharina Horstmann, Ludwigshafen (DE); Cornelia Katharina Dobner, Ludwigshafen (DE); Josef Macht, Mannheim (DE); Frank Rosowski, Mannheim (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 611 days.

(21) Appl. No.: 13/093,333

(22) Filed: Apr. 25, 2011

(65) Prior Publication Data

US 2011/0275856 A1  Nov. 10, 2011

Related U.S. Application Data

(60) Provisional application No. 61/353,230, filed on Jun. 10, 2010, provisional application No. 61/328,670, filed on Apr. 28, 2010.

(30) Foreign Application Priority Data

Apr. 28, 2010 (DE) .................... 10 2010 028 328
Jun. 10, 2010 (DE) .................... 10 2010 023 312

(51) Int. Cl.
| | |
|---|---|
| B01J 37/02 | (2006.01) |
| C07C 51/235 | (2006.01) |
| B01J 23/00 | (2006.01) |
| B01J 23/888 | (2006.01) |
| B01J 35/00 | (2006.01) |
| B01J 35/02 | (2006.01) |
| B01J 37/00 | (2006.01) |
| B01J 37/08 | (2006.01) |

(52) U.S. Cl.
CPC ............ *B01J 37/0219* (2013.01); *B01J 23/002* (2013.01); *B01J 23/8885* (2013.01); *B01J 35/008* (2013.01); *B01J 35/023* (2013.01); *B01J 35/026* (2013.01); *B01J 37/0221* (2013.01); *C07C 51/235* (2013.01); *B01J 37/0045* (2013.01); *B01J 37/08* (2013.01); *B01J 2523/00* (2013.01)

(58) Field of Classification Search
CPC ............ B01J 23/72; B01J 23/28; B01J 23/30; B01J 23/32; C01C 51/252
USPC .................. 502/300–355; 562/535
See application file for complete search history.

(56) References Cited

U.S. PATENT DOCUMENTS

| | | | |
|---|---|---|---|
| 4,305,843 A | 12/1981 | Krabetz et al. | |
| 5,677,261 A | 10/1997 | Tenten et al. | |
| 6,124,499 A * | 9/2000 | Hibst et al. | 562/535 |
| 6,395,936 B1 | 5/2002 | Arnold et al. | |
| 6,982,347 B2 * | 1/2006 | Dieterle et al. | 562/535 |
| 6,998,504 B1 | 2/2006 | Unverricht et al. | |
| 7,038,079 B2 * | 5/2006 | Hirao et al. | 562/535 |
| 7,157,597 B2 * | 1/2007 | Dieterle et al. | 562/535 |
| 7,217,680 B2 * | 5/2007 | Teshigahara et al. | 502/312 |
| 7,220,698 B2 * | 5/2007 | Yunoki et al. | 502/312 |
| 7,378,367 B2 * | 5/2008 | Yunoki et al. | 502/312 |
| 7,429,678 B2 * | 9/2008 | Tanimoto et al. | 562/535 |
| 7,456,129 B2 * | 11/2008 | Fukumoto et al. | 502/248 |
| 7,528,281 B2 * | 5/2009 | Yada et al. | 562/532 |
| 7,563,927 B2 * | 7/2009 | Ogawa et al. | 562/532 |
| 7,589,046 B2 * | 9/2009 | Dieterle et al. | 502/311 |
| 7,612,230 B2 * | 11/2009 | Shima et al. | 562/535 |
| 7,667,072 B2 * | 2/2010 | Yada et al. | 562/532 |
| 7,807,601 B2 * | 10/2010 | Wang et al. | 502/312 |
| 7,960,308 B2 * | 6/2011 | Fukumoto | 502/300 |
| 8,178,719 B2 * | 5/2012 | Shima et al. | 562/535 |
| 8,318,631 B2 * | 11/2012 | Cremer et al. | 502/312 |
| 2001/0003727 A1 * | 6/2001 | Tanimoto et al. | 502/304 |
| 2001/0004627 A1 * | 6/2001 | Tanimoto et al. | 502/439 |
| 2001/0009885 A1 * | 7/2001 | Hecquet et al. | 502/306 |

(Continued)

FOREIGN PATENT DOCUMENTS

| | | |
|---|---|---|
| DE | 199 27 624 A1 | 12/2000 |
| DE | 103 60 057 A1 | 7/2004 |
| DE | 10 2007 028 333 A1 | 12/2008 |
| EP | 0 015 569 A1 | 9/1980 |
| EP | 0 714 700 A2 | 6/1996 |
| WO | WO 95/11081 | 4/1995 |
| WO | WO 2006/094766 A1 | 9/2006 |

OTHER PUBLICATIONS

International Search Report issued Aug. 17, 2011, in Patent Application No. PCT/EP2011/056528.

*Primary Examiner* — Anthony J Zimmer
(74) *Attorney, Agent, or Firm* — Oblon, McClelland, Maier & Neustadt, L.L.P.

(57) ABSTRACT

An eggshell catalyst consisting of a hollow cylindrical support body of length 2 to 10 mm, external diameter 4 to 10 mm and wall thickness 1 to 4 mm, and an eggshell, applied to the outer surface of the support body, of catalytically active oxide material of the general formula I, $$Mo_{12}V_{2\ to\ 4}W_{0\ to\ 3}Cu_{0.8\ to\ 1.5}X^1_{0\ to\ 4}X^2_{0\ to\ 40}O_n \quad (I)$$

in which the variables are each defined as follows:
$X^1$ = one or more elements of the alkali metals and alkaline earth metals;
$X^2$ = one or more elements from the group of Si, Al, Ti and Zr; and
n = the stoichiometric coefficient of the element oxygen, which is determined by the stoichiometric coefficients of the elements other than oxygen and the charges thereof in I.

15 Claims, 2 Drawing Sheets

(56) References Cited

U.S. PATENT DOCUMENTS

| | | | |
|---|---|---|---|
| 2003/0065216 A1* | 4/2003 | Tanimoto et al. | 562/532 |
| 2003/0109381 A1* | 6/2003 | Ohishi et al. | 502/307 |
| 2003/0153786 A1* | 8/2003 | Tanimoto et al. | 562/535 |
| 2003/0229250 A1* | 12/2003 | Tanimoto et al. | 562/535 |
| 2004/0176641 A1* | 9/2004 | Tanimoto et al. | 562/547 |
| 2004/0250868 A1* | 12/2004 | Yada et al. | 141/1 |
| 2005/0176995 A1* | 8/2005 | Yunoki et al. | 562/535 |
| 2005/0215818 A1* | 9/2005 | Yunoki et al. | 562/547 |
| 2005/0261521 A1* | 11/2005 | Teshigahara et al. | 562/547 |
| 2006/0234861 A1* | 10/2006 | Fukumoto et al. | 502/232 |
| 2006/0258529 A1* | 11/2006 | Diefenbacher et al. | 502/321 |
| 2007/0149807 A1* | 6/2007 | Dieterle et al. | 562/535 |
| 2007/0149808 A1* | 6/2007 | Dieterle et al. | 562/535 |
| 2008/0161602 A1* | 7/2008 | Wang et al. | 562/549 |
| 2008/0214863 A1* | 9/2008 | Cremer et al. | 562/535 |
| 2008/0216915 A1* | 9/2008 | Yada et al. | 141/12 |
| 2008/0234522 A1* | 9/2008 | Yada et al. | 568/476 |
| 2008/0242815 A1* | 10/2008 | Fukumoto | 526/303.1 |
| 2008/0253943 A1* | 10/2008 | Yoda et al. | 422/219 |
| 2008/0307648 A1* | 12/2008 | Cremer et al. | 29/890 |
| 2009/0005593 A1* | 1/2009 | Yunoki et al. | 562/598 |
| 2009/0042723 A1* | 2/2009 | Wang et al. | 502/312 |
| 2009/0105507 A1* | 4/2009 | Dubois et al. | 568/594 |
| 2011/0105790 A1* | 5/2011 | Hagemeyer et al. | 562/598 |

* cited by examiner

EGGSHELL CATALYST CONSISTING OF A HOLLOW CYLINDRICAL SUPPORT BODY AND A CATALYTICALLY ACTIVE OXIDE MATERIAL APPLIED TO THE OUTER SURFACE OF THE SUPPORT BODY

DETAILED DESCRIPTION OF THE INVENTION

Figure 1:
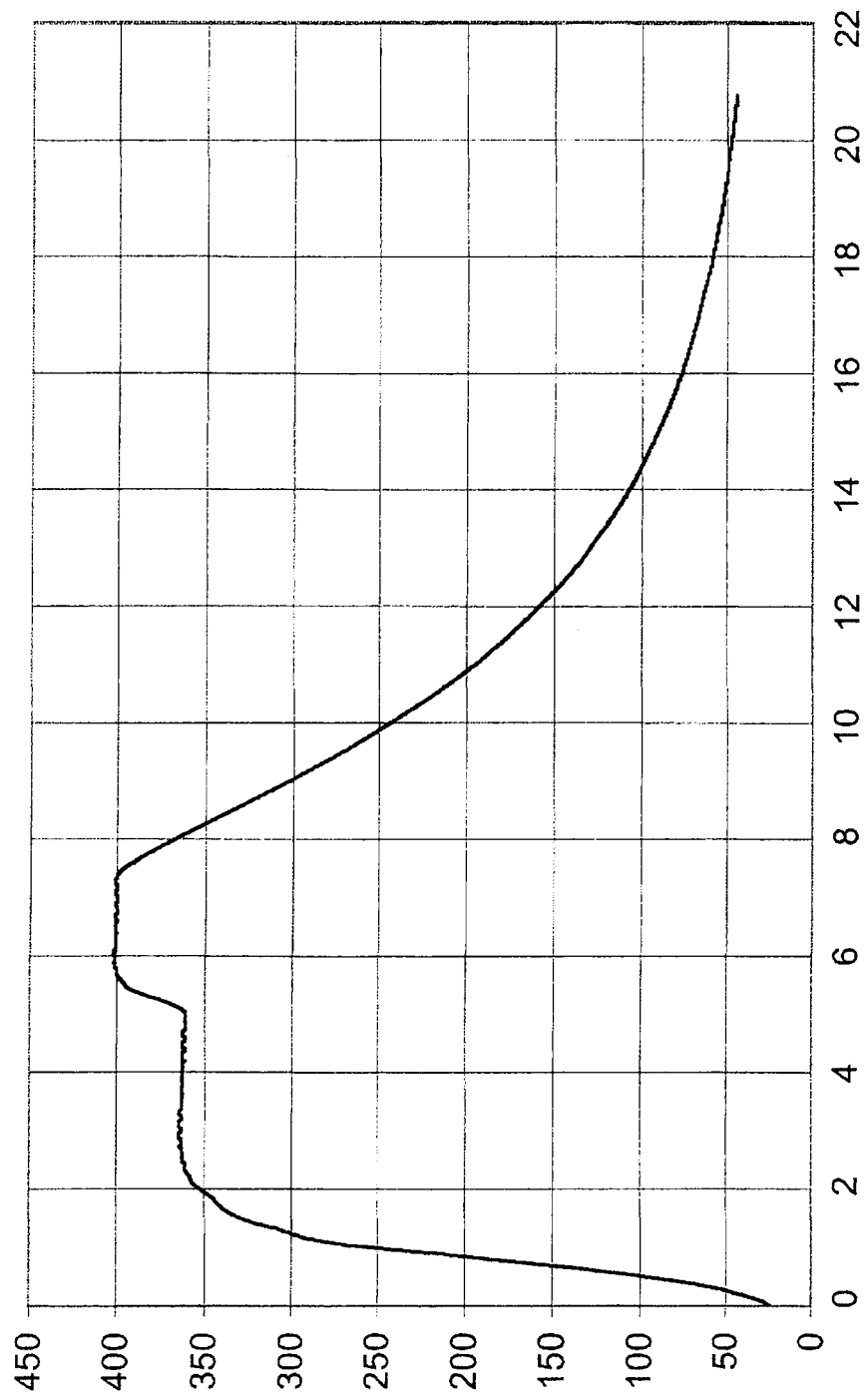
FIG. 1 shows the profile of the material temperature as a function of calcination time.

The present invention provides an eggshell catalyst consisting of a hollow cylindrical support body of length 2 to 10 mm, external diameter 4 to 10 mm and wall thickness 1 to 4 mm, and an eggshell, applied to the outer surface of the support body, of catalytically active oxide material of the general formula I

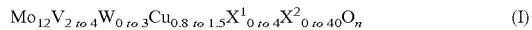  (I)

in which the variables are each defined as follows:

$X^1$=one or more elements of the alkali metals and alkaline earth metals;

$X^2$=one or more elements from the group of Si, Al, Ti and Zr; and n=the stoichiometric coefficient of the element oxygen, which is determined by the stoichiometric coefficients of the elements other than oxygen and the charges thereof in I.

Ring-shaped eggshell catalysts composed of a ring-shaped support body and an eggshell of catalytically active oxide material which comprises at least the elements Mo, V and Cu and has been applied to the outer surface of the support body are known (cf., for example, EP-A 714 700, DE-A 199 27 624 and DE-A 10360057). They are used principally as catalysts for the heterogeneously catalyzed partial gas phase oxidation of acrolein to acrylic acid. It is a characteristic feature that, in all illustrative embodiments of these ring-shaped eggshell catalysts, the molar ratio R formed from the molar amount of Cu present in the catalytically active oxide material ($m_{Cu}$) and the molar amount of V present in the catalytically active oxide material ($m_V$), as R=$m_{Cu}/m_V$, is at least 0.8.

However, a disadvantage of such ring-shaped eggshell catalysts when used as catalysts for the heterogeneously catalyzed partial gas phase oxidation of acrolein to acrylic acid is that they are not entirely satisfactory either in terms of the selectivity of acrylic acid formation ($S^{AS}$) or in terms of the activity thereof.

It was therefore an object of the present invention to provide improved ring-shaped eggshell catalysts composed of a ring-shaped support body and a shell of catalytically active oxide material which comprises at least the elements Mo, V and Cu and has been applied to the outer surface of the support body, which have an improved selectivity and a higher activity especially when used as catalysts for the heterogeneously catalyzed partial gas phase oxidation of acrolein to acrylic acid.

Accordingly, ring-shaped eggshell catalysts consisting of a hollow cylindrical (ring-shaped) support body of length 2 to 10 mm, external diameter 4 to 10 mm and wall thickness 1 to 4 mm, and an eggshell, applied to the outer surface of the support body, of catalytically active oxide material of the general formula I

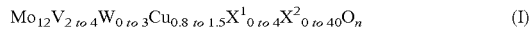  (I)

in which the variables are each defined as follows:

$X^1$=one or more elements of the alkali metals and alkaline earth metals;

$X^2$=one or more elements from the group of Si, Al, Ti and Zr; and n=the stoichiometric coefficient of the element oxygen, which is determined by the stoichiometric coefficients of the elements other than oxygen and the charges thereof in I;

are provided.

Advantageously in accordance with the invention, the stoichiometric coefficient of the element W in the general formula I is 0.2 to 3, preferably 0.5 to 2 and more preferably 0.75 to 1.5.

The stoichiometric coefficient of the element V in the general formula I is, advantageously in accordance with the invention, 2.5 to 3.5.

The stoichiometric coefficient of the element Cu in the general formula I is, preferably in accordance with the invention, 1.0 to 1.5.

Elements $X^1$ and $X^2$ need not necessarily be part of the catalytically active oxide materials of the general formula I.

Elements $X^2$ act like inert diluents within the catalytically active oxide materials of the general formula I. By virtue of the incorporation thereof into the catalytically active oxide materials of the general formula I, the volume-specific activity thereof can be adjusted to the desired level. Frequently, the stoichiometric coefficient of $X^2$ in the catalytically active oxide materials of the general formula I to be used in accordance with the invention is 0 to 15, or 0 to 8. More preferably, the catalytically active oxide materials of the general formula I for use in accordance with the invention do not comprise any element $X^2$. This statement also applies correspondingly to the elements $X^1$ which have a moderating influence on the catalytic activity. Frequently, the stoichiometric coefficient of $X^1$ in the catalytically active oxide materials of the general formula I for use in accordance with the invention will therefore be 0 to 2, or 0 to 1, or 0 to 0.2.

Eggshell catalysts preferred in accordance with the invention consist of a hollow cylindrical support body of length 3 to 6 mm, external diameter 4 to 8 mm and wall thickness 1 to 2 mm, and of an eggshell of catalytically active oxide material of the general formula I applied to the outer surface of the support body. Very particular preference is given to inventive eggshell catalysts in which the ring-shaped (hollow cylindrical) support body has the geometry 7 mm×3 mm×4 mm (external diameter×length×internal diameter).

The thickness of the eggshell of catalytically active oxide material applied to the hollow cylindrical support body in the inventive eggshell catalysts is, appropriately in application terms, generally 10 to 1000 μm. This eggshell thickness in inventive eggshell catalysts is preferably 10 to 500 μm, more preferably 100 to 500 μm and most preferably 200 to 300 μm.

Advantageously, the eggshell thickness viewed over a single eggshell catalyst is very substantially homogeneous. In the case of production of a relatively large production batch of inventive eggshell catalysts, the eggshell thickness viewed over several individual eggshell catalyst ring bodies is likewise very substantially homogeneous.

The ring-shaped support body of the inventive eggshell catalysts consists preferably of chemically inert material. As a result, the support bodies essentially do not intervene in the course of the gas phase oxidation which is catalyzed by the inventive eggshell catalysts. Useful such inert materials for the support bodies are, in accordance with the invention, especially aluminum oxide, silicon dioxide, silicates such as clay, kaolin, steatite, pumice, aluminum silicate and magnesium silicate, silicon carbide, zirconium dioxide and thorium dioxide (particular preference is given in accordance with the invention to ring-shaped support bodies of type C 220 steatite from CeramTec). The aforementioned materials may be porous or nonporous. Preference is given to support bodies with distinct surface roughness (for example hollow cylinders with a grit layer).

Inventive eggshell catalysts can be produced in different ways.

For example, it is possible first to prepare the catalytically active oxide material of the general formula I as such. Such a preparation is effected typically by obtaining, from suitable sources of the elemental constituents of the catalytically active oxide material, a very intimate, preferably finely divided dry mixture whose composition corresponds to the stoichiometry thereof (a precursor material), and calcining it (thermally treating it) at temperatures of 350 to 600° C. The calcination can be performed either under inert gas or under an oxidative atmosphere, for example air (or another mixture of inert gas and oxygen), or else under a reducing atmosphere (for example mixtures of inert gas and reducing gases such as $H_2$, $NH_3$, CO, methane and/or acrolein, or the reducing gases mentioned alone). The resulting catalytic activity generally exhibits an optimum depending on the oxygen content of the calcination atmosphere. The oxygen content of the calcination atmosphere is preferably 0.5 to 10% by volume, more preferably 1 to 5% by volume. Oxygen contents above and below the aforementioned limits normally reduce the resulting catalytic activity. The calcination time may be a few minutes to a few hours and typically decreases with the level of the calcination temperature. A calcination process which is very suitable in accordance with the invention is described, for example, by WO 95/11081.

Useful sources for the elemental constituents of the catalytically active oxide material of the general formula I are those compounds which are already oxides and/or those compounds which can be converted to oxides by heating, at least in the presence of oxygen. The starting compounds (sources) can be mixed intimately in dry or wet form. When the mixing is effected in dry form, the starting compounds are appropriately used in the form of fine powders and, after mixing and optional compaction, subjected to calcination. However, preference is given to effecting the intimate mixing in wet form. This typically involves mixing the starting compounds with one another in the form of an aqueous solution and/or suspension. Particularly intimate dry mixtures are obtained in the mixing process described when the starting materials are exclusively sources of the elemental constituents present in dissolved form.

The solvent used is preferably water. Subsequently, the resulting liquid (e.g. aqueous) material is dried, the drying process preferably being effected by spray drying of the liquid (e.g. aqueous) mixture with exit temperatures of 100 to 150° C. The drying gas stream is, appropriately in application terms, air or molecular nitrogen.

The catalytically active oxide material obtained after the calcination is subsequently converted to a fine powder, for example by grinding, which can then normally be applied to the outer surface of the support body with the aid of a liquid binder. The fineness of the catalytically active oxide material to be applied to the surface of the support body is of course matched to the desired eggshell thickness.

For example, the support bodies are moistened in a controlled manner with the liquid binder, for example by spraying, and the support bodies thus moistened are dusted with the finely divided catalytically active oxide material (cf., for example, EP-A 714700). Subsequently, the adhering liquid is at least partly removed from the moistened support body coated with active oxide material (for example passage of hot gas through; cf. WO 2006/094766). However, it is also possible to employ all other application processes acknowledged as prior art in EP-A 714700 for production of inventive eggshell catalysts. Useful liquid binders include, for example, water and aqueous solutions.

In principle, however, the procedure for preparation of inventive eggshell catalysts may also be first to apply finely divided precursor material to the surface of the support body, and to perform the calcination of the precursor material to give the catalytically active oxide material of the general formula I only subsequently, i.e. already on the surface of the support body.

Preferably in accordance with the invention, inventive catalysts will be obtained by the preparation method described in EP-A 714700 and detailed by way of example. An aqueous solution of 75% by weight of water and 25% by weight of glycerol is a preferred binder. The process for thermal treatment of the precursor material of a catalytically active oxide material will, advantageously in accordance with the invention, be performed by the procedure described in DE-A 10360057 and detailed by way of example. This uses the same sources of the elemental constituents as in DE-A 10360057, but in ratios corresponding to the inventive stoichiometry. The application process preferred in accordance with the invention for the catalytically active oxide material of the general formula I to the surface of the hollow cylindrical support bodies is likewise described in working examples 1 and 2 of DE-A 10360057.

Overall, inventive eggshell catalysts are most preferably prepared as described in working examples 1 and 2 of DE-A 10360057. Useful sources for the elemental constituent Cu for the preparation of inventive catalysts are especially copper (II) sulfate pentahydrate, copper(II) nitrate hydrate (Cu content=26.1% by weight) and copper(II) acetate monohydrate, among which preference is given to the latter. Ammonium metavanadate is the preferred vanadium source, and ammonium paratungstate heptahydrate is the preferred tungsten source. Appropriately in application terms, the Mo source used is ammonium heptamolybdate tetrahydrate. Other useful sources of the elemental constituents in addition to oxides are quite generally, in particular, halides, nitrates, formates, oxalates, acetates, carbonates and hydroxides.

Inventive eggshell catalysts (especially all eggshell catalysts prepared by way of example in this document) are especially suitable as catalysts for the heterogeneously catalyzed partial gas phase oxidation of acrolein to acrylic acid, and are notable especially for an improved selectivity $S^{AA}$ of acrylic acid formation and for an increased activity.

Against this background, inventive eggshell catalysts are particularly suitable not least in the case of acrolein-to-acrylic acid partial oxidations which are carried out at high acrolein velocities on the catalyst charge (e.g. ≥135 l (STP)/l·h to 350 or to 250 l (STP)/l·h). However, they can of course also be used at corresponding acrolein velocities of ≥50 l (STP)/l·h.

The term "space velocity" is used as defined in DE-A 19927624.

Advantageously, acrolein-to-acrylic acid partial oxidations are carried out with increased acrolein velocity on the catalyst charge using inventive eggshell catalysts also as described in DE-A 19927624 and in DE-A 10360057. Advantageously in accordance with the invention, the catalyst charge is configured such that the volume-specific activity of the fixed catalyst bed increases in flow direction of the reaction gas mixture (preferably by decreasing dilution of the inventive eggshell catalysts with inert shaped diluent bodies).

The reactor used to perform the heterogeneously catalyzed partial gas phase oxidation of acrolein to acrylic acid is, appropriately in application terms, a tube bundle reactor whose reaction tubes are filled with the fixed catalyst bed (cf. DE-A 19927624). When inventive eggshell catalysts are introduced into the tubes of the tube bundle reactor, the teaching of DE-A 102007028333 and the teaching of WO 2006/094766 will appropriately be followed.

In this document, the selectivity of acrylic acid formation ($S^{AA}$ (mol %)) is understood to mean:

$$S^{AA} = \frac{\text{number of moles of acrolein converted to acrylic acid}}{\text{total number of moles of acrolein converted}} \times 100.$$

(the conversions are each based on a single pass of the reaction gas mixture through the fixed catalyst bed).

An active material (catalyst) which leads to the same conversion at a lower temperature under otherwise unchanged reaction conditions possesses a higher activity.

The conversion $C^A$ of acrolein (mol %) is correspondingly defined as:

$$C^A = \frac{\text{number of moles of acrolein converted}}{\text{number of moles of acrolein used}} \times 100.$$

EXAMPLES AND COMPARATIVE EXAMPLES

A) Preparation of Eggshell Catalysts

Comparative Example 1A

Ring-shaped eggshell catalyst V1A with the catalytically active oxide material $Mo_{12}V_3W_{1.2}Cu_{2.4}O_n$ 259 g of copper(II) sulfate pentahydrate (Cu content=25.6% by weight) were dissolved in 2000 g of water at 70° C. within 1 h to give a solution I.

135 g of ammonium paratungstate heptahydrate (W content=71% by weight), 153 g of ammonium metavanadate (V content=43.5% by weight) and 920 g of ammonium heptamolybdate tetrahydrate (Mo content=54.5% by weight) were dissolved successively in 7000 g of water at 95° C. within 15 minutes to give a solution II. Subsequently, this solution II was heated to 98° C. within 3 min. Thereafter, the solution I at 70° C. was stirred gradually into the solution II at 98° C. within 5 minutes. The resulting aqueous suspension had a temperature of 95° C. and was stirred at this temperature for a further 5 minutes. The suspension was then spray-dried at an inlet temperature of 330° C. and an exit temperature of 106° C. in an air stream within 2 h (NIRO spray tower, spray head No. F0 A1). During the spray drying, the as yet unsprayed proportion of the suspension in each case continued to be stirred while maintaining 95° C. 900 g of the resulting spray powder which had been cooled to 25° C. were kneaded with 180 g of a 50% by weight aqueous acetic acid solution and an additional 170 g of water, both of which had a temperature of 25° C., with a Werner & Pfleiderer ZS1-80 kneader (kneading time: approx. 2 hours; kneading temperature: 30-35° C.).

Subsequently, the kneaded material was dried in a forced-air drying cabinet with a layer thickness of 2 cm at a temperature of 110° C. over 16 h.

700 g of the precursor material taken from the drying cabinet were calcined batchwise in a rotary tube furnace. The rotary tube furnace consisted of a furnace of length 162 cm and a rotary tube of length 209 cm passed through this furnace. The internal diameter of the rotary tube was 12.5 cm. The upper and lower 23.5 cm of the rotary tube projected out of the furnace. Over the entire calcination (including cooling), a gas stream of 240 l (STP)/h (the l (STP) are based on 25° C. and 1 bar) was passed through the rotary tube, which consisted of a mixture of air with molecular nitrogen, the molecular oxygen content of which was 1.9% by volume. The gas stream was supplied to the rotary tube furnace at a temperature of 25° C. The rotary tube itself was manufactured from stainless steel, and the angle of inclination of the rotary tube to the horizontal was=1.7°. The rotary tube rotated at 1 revolution/min. Support grids held the calcination material centrally at a length of ¼ of the total length of the rotary tube. Over the course of the calcination, the precursor material was heated first from 25° C. in an essentially linear manner to a material temperature of 300±2° C. within one hour and 15 minutes, then in an essentially linear manner to a material temperature of 350±2° C. within 45 minutes, and then in an essentially linear manner to a material temperature of 362±2° C. within 30 minutes. Over the next 2 hours and 35 minutes, this material temperature was maintained. Then the precursor material was heated first in an essentially linear manner to a material temperature of 395±2° C. within 25 min and then in an essentially linear manner to a material temperature of 400±2° C. within a further 10 min, held at this temperature over the course of a further hour and 45 minutes and then cooled to 44±2° C. by switching off the furnace while maintaining the rotation of the rotary tube over the course of approx. 13 h, and taken from the rotary tube at this temperature. FIG. 1 shows the measured profile of the material temperature (in ° C. as the ordinate) as a function of calcination time (in hours (h) as the abscissa).

The catalytically active oxide material taken from the rotary tube furnace was subsequently ground in a Retsch ZM 200 mill to a fine powder, of which 50% of the powder particles passed through a sieve of mesh size 1 to 10 μm, and in which the numerical proportion of particles having a longest dimension above 50 μm was less than 1%.

Figure 2:
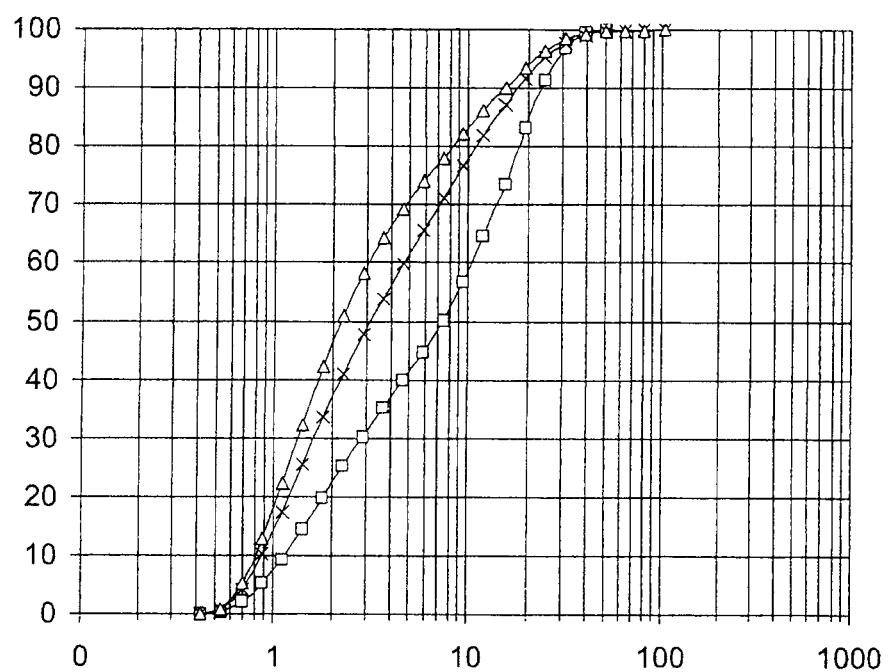
FIG. 2 shows a favorable size distribution of ground catalytically active oxide material powder.

A size distribution of the particles of the aforementioned ground catalytically active oxide material powder, said size distribution being favorable for the comparative examples and working examples of this document, is shown by FIG. 2 of this application (the abscissa shows, in a logarithmic plot (on a logarithmic scale), the particle diameter (the particle dimension) in μm, and the ordinate shows the particular corresponding cumulative proportion of the particles in % by volume (the ordinate value of one point on the distribution curve shows the X % of the total particle volume which consists of particles having the particle dimension assigned to this point on the abscissa or having a smaller particle dimension; in other words, (100−X)% of the total particle volume consist of particles having a greater particle dimension (having a greater particle diameter)). The underlying test method is laser diffraction. This involves conducting the particular fine powder through a dispersing channel into the Sympatec RODOS dry disperser (Sympatec GmbH, System-Partikel-Technik, Am Pulverhaus 1, D-38678 Clausthal-Zellerfeld), dry-dispersing it therein with compressed air and blowing it into the test cell in a free jet. In this cell, the Malvern Mastersizer S laser diffraction spectrometer (Malvern Instruments, Worcestershire WR14 1AT, United Kingdom) is used to determine the volume-based particle diameter distribution to ISO 13320 (obscuration 3-7%). The intensity of the dispersion of the dry powder during the analysis is determined by the dispersion pressure employed (FIG. 2: squares=1.2 bar; crosses=2.0 bar; triangles=3.5 bar; each as the absolute pressure) of the compressed air employed as the propellant gas.

The ground catalytically active oxide material powder was used, as described in S1 of EP-B 714700, to coat 800 g of ring-shaped support bodies (external diameter 7 mm, length 3 mm, internal diameter 4 mm, C 220 steatite from CeramTec with a surface roughness $R_Z$ of 45 μm (grit layer)). The total pore volume of the support body, based on the volume of the support body material, was 1% by volume. The binder was an aqueous solution composed of 75% by weight of water and 25% by weight of glycerol. The coating was effected in a rotating coating drum (internal diameter=25.5 cm; 36 rpm) which had been filled with the support bodies. About 60 ml of liquid binder were sprayed onto the support bodies through a nozzle (nozzle diameter=1 mm) within 60 min (the exact amount of binder in each case was such that no adhering pairs formed, but the total amount of powder was absorbed onto the surface of the support bodies without occurrence of powder agglomeration). At the same time, 205 g of the ground catalytically active oxide material powder were metered in continuously over the same period by means of a delivery screw outside the spray cone of the atomizer nozzle. During the coating, the powder supplied was taken up completely onto the surface of the support bodies. No agglomeration of the fine oxidic active material was observed.

Subsequently, the coated rings were kept (demoistened) at a temperature of 300° C. in a forced-air drying cabinet for 2 h.

The eggshell catalysts taken from the forced-air drying cabinet had, based on the total mass thereof, an oxidic active material content of approx. 20% by weight. The active material eggshell thickness was 150 to 250 μm.

Comparative Example V2A

The ring-shaped eggshell catalyst V2A with the catalytically active oxide material $Mo_{12}V_3W_{1.2}Cu_{2.4}O_n$ was prepared as in V1A, except that 255 g of copper(II) nitrate hydrate (Cu content=26.1% by weight) were used as the Cu source instead of the 259 g of copper(II) sulfate pentahydrate.

Comparative Example V3A

The ring-shaped eggshell catalyst V3A with the catalytically active oxide material $Mo_{12}V_3W_{1.2}Cu_{2.4}O_n$ was prepared as in V1A, except that 210 g of copper(II) acetate monohydrate (Cu content=31.7% by weight) were used as the Cu source instead of the 259 g of copper(II) sulfate pentahydrate.

Working Example 1A

The ring-shaped eggshell catalyst A1A with the catalytically active oxide material $Mo_{12}V_3W_{1.2}Cu_{1.2}O_n$ was prepared as in V1A, except that 134.0 g of copper(II) sulfate pentahydrate, 139.7 g of ammonium paratungstate heptahydrate, 158 g of ammonium metavanadate and 950 g of ammonium heptamolybdate tetrahydrate were used.

Working Example 2A

The ring-shaped eggshell catalyst A2A with the catalytically active oxide material $Mo_{12}V_3W_{1.2}Cu_{1.2}O_n$ was prepared as in V2A, except that 127.3 g of copper(II) nitrate trihydrate were used as the Cu source.

Working Example 3A

The ring-shaped eggshell catalyst A3A with the catalytically active oxide material $Mo_{12}V_3W_{1.2}Cu_{1.2}O_n$ was prepared as in V3A, except that 104.8 g of copper(II) acetate monohydrate were used as the Cu source.

B) Testing of Eggshell Catalysts V1A to A3A as Catalysts for the Heterogeneously Catalyzed Partial Gas Phase Oxidation of Acrolein to Acrylic Acid A reaction tube (V2A steel; external diameter 30 mm; wall thickness 2 mm; internal diameter 26 mm; length 440 cm; a thermal tube centered in the middle of the reaction tube cross section and conducted along the reaction tube (external diameter 4 mm) for accommodating a thermocouple) was charged from the bottom upward in each case as follows:
Section 1: length 25 cm
    catalyst support made from V2A steel for accommodating the fixed catalyst bed;
Section 2: length 55 cm
    preliminary bed of steatite spheres having a diameter of 4 to 5 mm (C220 steatite from CeramTec);
Section 3: length 100 cm
    fixed catalyst bed composed of a homogeneous mixture consisting of 30% by weight of steatite rings of geometry 7 mm×3 mm×4 mm (external diameter×length× internal diameter; C220 steatite from CeramTec) and 70% by weight of the particular eggshell catalyst;
Section 4: length 200 cm
    fixed catalyst bed consisting exclusively of the eggshell catalyst used in section 3 in each case;
Section 5: 60 cm of empty tube.

A reaction gas mixture was conducted through the particular reaction tube charged as described above, flowing from the bottom upward through the reaction tube, and had the following contents:
4.6% by volume of acrolein,
0.1% by volume of propene,
0.2% by volume of acrylic acid,
5.4% by volume of $O_2$,
1.6% by volume of CO and $CO_2$,
81.9% by volume of $N_2$ and
6.2% by volume of $H_2O$.

The feed temperature of the reaction gas mixture (at the inlet into the reaction tube) was 210° C., and the space velocity of acrolein on the fixed catalyst bed (as defined in DE-A 19927624) was 85 l (STP)/l·h.

The temperature of the reaction tube was controlled over the length thereof (apart from the last 20 cm of the tube in section 1 and the 60 cm of empty tube in section 5) in each case by means of a salt bath (53% by weight of potassium nitrate, 40% by weight of sodium nitrite and 7% by weight of sodium nitrate, 220 kg of salt melt) which was not pumped in circulation but was sparged with molecular nitrogen by the principle of the airlift pump and was externally electrically heated, and in each case had the salt bath temperature TB (° C.) required in a constant manner over the time and the tube length. The nitrogen stream bubbled into the salt bath at the bottom with a temperature of 25° C. was 300 l (STP)/h (the bubbling was effected by means of six nozzles distributed homogeneously over the cross section of the salt bath at 50 l (STP)/h per nozzle). The salt bath temperature TB (° C.) in all cases was set so as to result in an acrolein conversion of approx. 99.5 mol % based on single pass of the reaction gas mixture through the fixed catalyst bed. Along the reaction tube, the salt bath temperature did not change as a result of additional heating (more heat was released from the salt bath than transferred from the reaction tube to the salt bath).

Table 1 below shows the results as a function of the eggshell catalyst used after 100 operating hours in each case:

TABLE 1

| Eggshell catalyst | $T^B$ (° C.) | $C^A$ (mol %) | $S^{AA}$ (mol %) |
|---|---|---|---|
| V1A | 261 | 99.4 | 95.1 |
| V2A | 294 | 99.5 | 95.6 |
| V3A | 258 | 99.4 | 96.0 |
| A1A | 251 | 99.6 | 96.8 |
| A2A | 264 | 99.5 | 97.3 |
| A3A | 257 | 99.5 | 97.5 |

The results shown in Table 1 show that, irrespective of the Cu source used, the stoichiometry $Mo_{12}V_3W_{1.2}Cu_{1.2}O_n$ of the catalytically active oxide material compared to the stoichiometry $Mo_{12}V_3W_{1.2}Cu_{2.4}O_n$ causes markedly higher selectivities of acrylic acid formation.

Furthermore, the results in Table 1 show that the best $S^{AA}$ values are obtained when copper(II) acetate monohydrate is used as the Cu source.

Otherwise, the inventive eggshell catalysts show comparatively elevated activities.

C) Preparation of Eggshell Catalysts

Comparative Example 1B

Ring-shaped eggshell catalyst V1B with the catalytically active oxide material $Mo_{12}V_3W_{1.2}Cu_{0.6}O_n$ 23.9 g of copper(II) acetate monohydrate (Cu content=31.7% by weight) were dissolved in 1600 g of water at 25° C. while stirring to give a solution I.

420 g of ammonium heptamolybdate tetrahydrate (Mo content=54.5% by weight) were dissolved in 3780 g of water at 90° C. within 5 min. Subsequently, while maintaining 90° C., 69.1 g of ammonium metavanadate (V content=43.5% by weight) were added and the resulting solution was stirred at 90° C. for a further 30 minutes. Then 61.8 g of ammonium paratungstate heptahydrate (W content=71% by weight) were added and the resulting solution II was stirred at 90° C. for a further 40 minutes. Subsequently, the solution II was cooled to 80° C. within 10 minutes.

The solution I at 25° C. was stirred into the solution II at 80° C. within 5 minutes. The resulting mixture had a temperature of 75° C. Then 765 g of a 25% by weight aqueous $NH_3$ solution at a temperature of 25° C. were added to the mixture at 75° C. within 15 min. The resulting aqueous solution had a temperature of 79° C. and was heated to 80° C. within 2 min, and stirred at this temperature for a further 10 minutes. The solution was subsequently spray dried in an air stream at an inlet temperature of 350° C. and an exit temperature of 120° C. within 2 h (NIRO spray tower, spray head No. F0 A1). During the spray drying, the proportion of the suspension which was yet to be sprayed in each case continued to be stirred while maintaining 80° C.

900 g of the resulting spray powder cooled to 25° C. were kneaded with 180 g of a 50% by weight aqueous acetic acid solution and an additional 90 g of water, both of which had a temperature of 25° C., with a Werner & Pfleiderer ZS1-80 kneader (kneading time: approx. 2 hours; kneading temperature: 30-35° C.).

Subsequently, the kneaded material was dried in a forced-air drying cabinet with a layer thickness of approx. 2 cm at a temperature of 110° C. over the course of 16 h.

700 g of the precursor material taken from the drying cabinet were calcined in a rotary tube furnace. The rotary tube furnace consisted of a furnace of length 162 cm and a rotary tube passed through this furnace of length 209 cm. The internal diameter of the rotary tube was 12.5 cm. The upper and lower 23.5 cm of the rotary tube projected out of the furnace. Over the course of the entire calcination (including cooling), a gas stream of 240 l (STP)/h (the l (STP) are based on 25° C. and 1 bar) was passed through the rotary tube, which consisted of a mixture of air with molecular nitrogen, the molecular oxygen content of which was 2.2% by volume. The gas stream was fed to the rotary tube furnace at a temperature of 25° C. The rotary tube itself was manufactured from stainless steel, and the angle of inclination of the rotary tube to the horizontal was 1.7°. The rotary tube rotated at 1 revolution/min. Support grids held the calcination material centrally at a length of ¼ of the total length of the rotary tube.

Over the course of the calcination, the precursor material was heated first from 25° C. in an essentially linear manner to a material temperature of 300±2° C. within one hour and 15 minutes, then in an essentially linear manner to a material temperature of 350±2° C. within 45 minutes, and then in an essentially linear manner to a material temperature of 362±2° C. within 30 minutes. Over the course of the next 2 hours and 35 minutes, this material temperature was maintained. Then the precursor material was heated first in an essentially linear manner to a material temperature of 395±2° C. within 25 min and subsequently in an essentially linear manner to a material temperature of 400±2° C. within a further 10 min, held at this temperature over the course of a further hour and 45 minutes, and then cooled to 44±2° C. by switching off the furnace while maintaining the rotation of the rotary tube over the course of approx. 13 h, and taken from the rotary tube at this temperature. FIG. 1 shows the profile of the material temperature as a function of the calcination time.

The catalytically active oxide material taken from the rotary tube furnace was subsequently ground in a Retsch ZM 200 mill to give a fine powder, of which 50% of the powder particles passed through a sieve of mesh size 1 to 10 μm, and in which the numerical proportion of particles having a longest dimension above 50 μm was less than 1%.

The ground catalytically active oxide material powder was used, as described in S1 of EP-B 714700, to coat 800 g of ring-shaped support bodies (external diameter 7 mm, length 3 mm, internal diameter 4 mm, C 220 steatite from CeramTec with a surface roughness $R_Z$ of 45 μm (grit layer)). The total pore volume of the support body based on the volume of the support body material was 1% by volume. The binder was an aqueous solution composed of 75% by weight of water and 25% by weight of glycerol. The coating was effected in a rotating coating drum (36 rpm) which had been filled with the support bodies. Approx. 90 ml of the liquid binder were sprayed onto the support bodies via a nozzle (nozzle diameter=1 mm) within 60 min (the exact amount of binder in each case was such that no adhering pairs were formed, but the total amount of powder was taken up onto the surface of the support bodies without occurrence of powder agglomeration). At the same time, 205 g of the ground catalytically active oxide material powder were metered in continuously in the same space via a vibrating chute outside the spray cone of the atomizer nozzle. During the coating, the powder supplied was taken up completely onto the surface of the support bodies. No agglomeration of the fine oxidic active material was observed.

Subsequently, the coated rings were kept (demoistened) at a temperature of 300° C. in a forced-air drying cabinet for 2 h.

The eggshell catalysts taken from the forced-air drying cabinet had, based on their total mass, an oxidic active material content of approx. 20% by weight. The active material eggshell thickness was 150 to 250 µm.

Comparative Example 2B

The ring-shaped eggshell catalyst V2B with the catalytically active oxide material $Mo_{12}V_3W_{1.2}Cu_{1.8}O_n$ was prepared as in V1B, except that 71.8 g of rather than 23.9 g of copper(II) acetate monohydrate (Cu content=31.7% by weight) were used.

Comparative Example 3B

The ring-shaped eggshell catalyst V3B with the catalytically active oxide material $Mo_{12}V_3W_{1.2}Cu_{2.4}O_n$ was prepared as in V1B, except that 96.6 g of rather than 23.9 g of copper(II) acetate monohydrate (Cu content=31.7% by weight) were used.

Working Example 1B

The ring-shaped eggshell catalyst A1B with the catalytically active oxide material $Mo_{12}V_3W_{1.2}Cu_{1.2}O_n$ was prepared as in V1B, except that 47.8 g of rather than 23.9 g of copper(II) acetate monohydrate (Cu content=31.7% by weight) were used.

D) Testing of the Eggshell Catalysts V1B to V3B and A1B as Catalysts for the Heterogeneously Catalyzed Partial Gas Phase Oxidation of Acrolein to Acrylic Acid A reaction tube (V2A steel; external diameter 30 mm; wall thickness 2 mm; internal diameter 26 mm; length 464 cm) was charged from the top downward as follows:
Section 1: length 80 cm
  empty tube;
Section 2: length 60 cm
  preliminary bed of steatite rings of geometry 7 mm×3 mm×4 mm (external diameter×length×internal diameter; C 220 steatite from CeramTec);
Section 3: length 100 cm
  fixed catalyst bed composed of a homogeneous mixture consisting of 20% by weight of steatite rings of geometry 7 mm×3 mm×4 mm (external diameter×length× internal diameter; C 220 steatite from CeramTec) and 80% by weight of the particular eggshell catalyst;
Section 4: length 200 cm
  fixed catalyst bed consisting exclusively of the eggshell catalyst used in section 3 in each case;
Section 5: length 10 cm
  downstream bed of the same steatite rings as in section 2;
Section 6: length 14 cm
  catalyst support made of V2A steel for accommodating the fixed catalyst bed.

A reaction gas mixture was conducted through the particular reaction tube charged as described above, flowing through the reaction tube from the top downward, and had the following contents:
4.25% by volume of acrolein,
0.3% by volume of propene,
0.2% by volume of propane,
0.3% by volume of acrylic acid,
5.15% by volume of $O_2$,
0.5% by volume of CO and $CO_2$,
7% by volume of $H_2O$ and
82.3% by volume of $N_2$.

The feed temperature of the reaction gas mixture (at the inlet into the reaction tube) was 210° C., and the space velocity of acrolein on the fixed catalyst bed (as defined in DE-A 19927624) was 80 l (STP)/l·h.

Over the length of the reaction tube (apart from the last 10 cm of the empty tube in section 1 and the last 3 cm of the tube in section 6), a stirred and externally electrically heated salt bath (mixture of 53% by weight of potassium nitrate, 40% by weight of sodium nitrite and 7% by weight of sodium nitrate, 50 kg of salt melt) flowed around it in each case (the flow rate in the tube was 3 m/s). The salt bath temperature $T^B$ (° C.) (with which the salt bath was supplied) was adjusted in all cases so as to result in an acrolein conversion based on single pass of the reaction gas mixture through the fixed catalyst bed of 99.3 mol %. The salt bath temperature along the reaction tube did not change owing to additional heating (more heat was emitted from the salt bath than released to the salt bath by the reaction tube).

Table 2 below shows the results as a function of the eggshell catalyst used after 100 operating hours:

TABLE 2

| Eggshell catalyst | $T^B$ (° C.) | $C^A$ (mol %) | $S^{AA}$ (mol %) |
|---|---|---|---|
| V1B | 270 | 99.3 | 96.9 |
| V2B | 261 | 99.3 | 96.2 |
| V3B | 275 | 99.3 | 95.4 |
| A1B | 256 | 99.3 | 96.9 |

The results shown in Table 2 show that the stoichiometry $Mo_{12}V_3W_{1.2}Cu_{1.2}O_n$ has the highest activity. At the same time, this stoichiometry is at the peak with regard to the target product selectivity achieved.

E) Preparation of Eggshell Catalysts

Comparative Example 1C

The annular eggshell catalyst V1C with the catalytically active oxide material $Mo_{12}V_3W_{1.2}Cu_{2.4}O_n$ was prepared as in comparative example 3B, but with the difference that the gas stream passed through the rotary tube over the entire calcination comprised not 2.2% by volume but 2.6% by volume of molecular oxygen.

Working Example 10

The annular eggshell catalyst A1C with the catalytically active oxide material $Mo_{12}V_3W_{1.2}Cu_{1.2}O_n$ was prepared as in working example 1B, but with the difference that the gas stream passed through the rotary tube over the entire calcination comprised not 2.2% by volume but 2.6% by volume of molecular oxygen.

F) Testing of Eggshell Catalysts V1C and A1C as Catalysts for the Heterogeneously Catalyzed Partial Gas Phase Oxidation of Acrolein to Acrylic Acid The testing was effected as in B), except that the contents of the reaction gas mixture flowing through the reaction tube from the bottom were as follows:
4.6% by volume of acrolein,
0.1% by volume of propene, 0.3% by volume of acrylic acid,
5.6% by volume of $O_2$,
1.3% by volume of CO and $CO_2$,
82.1% by volume of $N_2$ and
6.0% by volume of $H_2O$.

The space velocity of acrolein on the fixed catalyst bed (as defined in DE-A 19927624) was 84 l (STP)/l·h.

Table 3 below shows the results as a function of the eggshell catalyst used after 100 operating hours in each case:

TABLE 3

| Eggshell catalyst | $T^B$ (° C.) | $C^A$ (mol %) | $S^{AA}$ (mol %) |
|---|---|---|---|
| V1C | 260 | 99.5 | 95.8 |
| A1C | 258 | 99.5 | 96.4 |

Remarkably, the temperature measured by means of a thermocouple in the thermal tube in the case of use of the eggshell catalyst A1C exhibits two temperature maxima along the thermal tube in flow direction of the reaction gas mixture. The first temperature maximum is 287° C. and is in charge section 3 at the position "150 cm from the lower end of the reaction tube". The second temperature maximum is 291° C. and is in charge section 4 at the position "210 cm from the lower end of the reaction tube".

In contrast, the temperature measured by means of a thermocouple in the thermal tube in the case of use of the eggshell catalyst V1C likewise exhibits two temperature maxima along the thermal tube in flow direction. However, the first temperature maximum (in flow direction) in this case is 290° C., and the second temperature maximum is 287° C. (the positions of the temperature maxima are at the same points as in the case of use of the eggshell catalyst A1C). It is surprising that use of the eggshell catalyst A1C results in a higher target product selectivity, even though the second temperature maximum in flow direction of the reaction gas mixture in this case has the higher temperature.

When, in the case of a reaction gas mixture composition of
5% by volume of acrolein,
0.1% by volume of propene,
0.4% by volume of acrylic acid,
5.5% by volume of $O_2$,
1.4% by volume of CO and $CO_2$,
80.9% by volume of $N_2$ and
6.7% by volume of $H_2O$,
under otherwise identical operating conditions, in the case of eggshell catalyst A1C, the space velocity of acrolein on the fixed catalyst bed was raised to 104 l (STP)/l·h, the following results were obtained after 100 operating hours:

| $T^B$ (° C.) | $C^A$ (mol %) | $S^{AA}$ (mol %) |
|---|---|---|
| 259 | 99.5 | 96.2 |

In this case too, temperature maxima are present in the thermal tube at the positions "150 cm from the lower end of the reaction tube" and "210 cm from the lower end of the reaction tube". The first maximum in flow direction is now 302° C. and the second temperature maximum in flow direction is now 294° C.

These results indicate that the stoichiometry $Mo_{12}V_3W_{1.2}Cu_{1.2}O_n$, even in the case of a comparatively elevated acrolein space velocity, still ensures a higher selectivity of acrylic acid formation than the stoichiometry $Mo_{12}V_3W_{1.2}Cu_{2.4}O_n$ at a comparatively lower acrolein space velocity.

U.S. Provisional Patent Applications No. 61/328,670, filed Apr. 28, 2010, and No. 61/353,230, filed Jun. 10, 2010, are incorporated into the present application by literature reference.

With regard to the abovementioned teachings, numerous changes and deviations from the present invention are possible. It can therefore be assumed that the invention, within the scope of the appended claims, can be performed differently than the way described specifically herein.

The invention claimed is:

1. An eggshell catalyst comprising:
a hollow cylindrical support body of length 2 to 10 mm, external diameter 4 to 10 mm and wall thickness 1 to 4 mm, and
an eggshell, applied to an outer surface of the support body, of catalytically active oxide material of formula I, $$Mo_{12}V_{2.5\ to\ 3.5}W_{0.5\ to\ 2}Cu_{1.0\ to\ 1.5}X^1_{0\ to\ 4}X^2_{0\ to\ 40}O_n \quad (I)$$
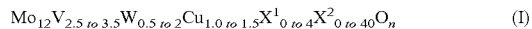

wherein $X^1$ is at least one selected from the group consisting of alkali metals and alkaline earth metals;
$X^2$ is at least one selected from the group consisting of Si, Al, Ti and Zr; and
n is a stoichiometric coefficient of the element oxygen, which is determined by stoichiometric coefficients of elements other than oxygen and charges thereof in formula I.

2. The eggshell catalyst according to claim 1, wherein a stoichiometric coefficient of W in formula I is 0.75 to 1.5.

3. The eggshell catalyst according to claim 1, wherein
the length of the hollow cylindrical support body is 3 to 6 mm,
the external diameter of the hollow cylindrical support body is 4 to 8 mm, and
the wall thickness of the hollow cylindrical support body is 1 to 2 mm.

4. The eggshell catalyst according to claim 1, wherein a thickness of the eggshell of catalytically active oxide material applied to the hollow cylindrical support body is 10 to 1000 µm.

5. A process for preparing acrylic acid, the process comprising:
catalytically oxidizing acrolein in a gas phase over a fixed catalyst bed,
wherein the fixed catalyst bed comprises the eggshell catalyst according to any of claims 1, 2, 3, and 4.

6. The process according to claim 5,
wherein an hourly space velocity of acrolein on the fixed catalyst bed is 50 to 350 l (STP)/l·h.

7. The eggshell catalyst according to claim 1, wherein a thickness of the eggshell of catalytically active oxide material applied to the hollow cylindrical support body is 10 to 500 µm.

8. The eggshell catalyst according to claim 1, wherein a thickness of the eggshell of catalytically active oxide material applied to the hollow cylindrical support body is 100 to 500 µm.

9. The eggshell catalyst according to claim 1, wherein a thickness of the eggshell of catalytically active oxide material applied to the hollow cylindrical support body is 200 to 300 µm.

10. A process for preparing acrylic acid by catalytically oxidizing acrolein in a gas phase over a fixed catalyst bed,
wherein the fixed catalyst bed comprises the eggshell catalyst according to claim 1, and
wherein an hourly space velocity of acrolein on the fixed catalyst bed is 135 to 250 l (STP)/l·h.

11. An eggshell catalyst consisting of:
a hollow cylindrical support body of length 2 to 10 mm, external diameter 4 to 10 mm and wall thickness 1 to 4 mm, and
an eggshell, applied to an outer surface of the support body, of catalytically active oxide material of formula I, $$Mo_{12}V_{2.5\ to\ 3.5}W_{0.5\ to\ 2}Cu_{1.0\ to\ 1.5}X^1_{0\ to\ 4}X^2_{0\ to\ 40}O_n \quad (I)$$

wherein
$X^1$ is at least one selected from the group consisting of alkali metals and alkaline earth metals;
$X^2$ is at least one selected from the group consisting of Si, Al, Ti and Zr; and
n is a stoichiometric coefficient of the element oxygen, which is determined by stoichiometric coefficients of elements other than oxygen and charges thereof in formula I.

12. The eggshell catalyst according to claim 11, wherein a ratio of the stoichiometric coefficient of Cu to the stoichiometric coefficient of V is from 0.29 to 0.6.

13. The eggshell catalyst according to claim 1, wherein a ratio of the stoichiometric coefficient of Cu to the stoichiometric coefficient of V is from 0.29 to 0.6.

14. An eggshell catalyst comprising:
a hollow cylindrical support body of length 2 to 10 mm, external diameter 4 to 10 mm and wall thickness 1 to 4 mm, and
an eggshell, applied to an outer surface of the support body, of catalytically active oxide material of formula I, $$Mo_{12}V_{2.5\ to\ 3.5}W_0Cu_{1.0\ to\ 1.5}X^1_{0\ to\ 4}X^2_{0\ to\ 40}O_n \quad (I)$$

wherein
$X^1$ is at least one selected from the group consisting of alkali metals and alkaline earth metals;
$X^2$ is at least one selected from the group consisting of Si, Al, Ti and Zr; and
n is a stoichiometric coefficient of the element oxygen, which is determined by stoichiometric coefficients of elements other than oxygen and charges thereof in formula I.

15. An eggshell catalyst consisting of:
a hollow cylindrical support body of length 2 to 10 mm, external diameter 4 to 10 mm and wall thickness 1 to 4 mm, and
an eggshell, applied to an outer surface of the support body, of catalytically active oxide material of formula I, $$Mo_{12}V_{2.5\ to\ 3.5}W_0Cu_{1.0\ to\ 1.5}X^1_{0\ to\ 4}X^2_{0\ to\ 40}O_n \quad (I)$$

wherein
$X^1$ is at least one selected from the group consisting of alkali metals and alkaline earth metals;
$X^2$ is at least one selected from the group consisting of Si, Al, Ti and Zr; and
n is a stoichiometric coefficient of the element oxygen, which is determined by stoichiometric coefficients of elements other than oxygen and charges thereof in formula I.

* * * * *